United States Patent
Wang et al.

(10) Patent No.: US 7,847,242 B2
(45) Date of Patent: Dec. 7, 2010

(54) PULSE HEATING-TIME OF FLIGHT MASS SPECTROMETRIC GAS ELEMENTS ANALYZER

(75) Inventors: Haizhou Wang, Beijing (CN); Peng Wang, Beijing (CN); Xuejing Yang, Beijing (CN); Zhigang Yang, Beijing (CN); Yuexiang Yan, Beijing (CN); Shaocheng Hu, Beijing (CN); Hongquan Ma, Beijing (CN); Hongwei Li, Beijing (CN)

(73) Assignee: Central Iron & Steel Research Institute, Beijing (CN)

( * ) Notice: Subject to any disclaimer, the term of this patent is extended or adjusted under 35 U.S.C. 154(b) by 220 days.

(21) Appl. No.: 12/259,502

(22) Filed: Oct. 28, 2008

(65) Prior Publication Data

US 2009/0121129 A1    May 14, 2009

(30) Foreign Application Priority Data

Oct. 29, 2007   (CN)   .................. 2007 1 0176455

(51) Int. Cl.
 *H01J 49/40*   (2006.01)
 *B01D 59/44*   (2006.01)
(52) U.S. Cl. ..................... 250/287; 250/288
(58) Field of Classification Search ........... 250/281, 250/282, 286–288, 299, 423 R, 424, 425
See application file for complete search history.

(56) References Cited

U.S. PATENT DOCUMENTS

| | | | |
|---|---|---|---|
| 6,573,493 B1 * | 6/2003 | Futami et al. | 250/288 |
| 2009/0032695 A1 * | 2/2009 | Kaye et al. | 250/281 |
| 2009/0056537 A1 * | 3/2009 | Neumann | 95/35 |
| 2009/0094893 A1 * | 4/2009 | Neumann | 48/62 R |

OTHER PUBLICATIONS

Wang, et al., A novel assembly gas analyzer for metallurgical materials by inert gas fusion & time-of-flight mass spectrometry, Metallurgical Analysis 28, Suppl. 1, pp. 109-119 (Nov. 2008).

* cited by examiner

*Primary Examiner*—Bernard E Souw
(74) *Attorney, Agent, or Firm*—Perkins Coie LLP

(57) ABSTRACT

A pulse heating—time of flight mass spectrometric gas elements analyzer, which involves the chemical analysis field of inorganic materials, and comprises of a pulse heating electrode furnace, a sample charging system, a purification device, a time-of-flight mass spectrometer, a signal acquisition and data processing system, and an automatic control system. Said electrode furnace and sample charging system are united as one via upper/lower electrodes and pneumatic cylinders, to form a closed hearth. Said electrode furnace, purification device and time-of-flight mass spectrometer are interconnected through the gas pipelines: the purified inert carrier gas comes into the hearth from its top, carrying out the gas components released from sample fusion, and upon re-purification, comes into the time-of-flight mass spectrometer; said signal acquisition and data processing system is connected to the detector of the said mass spectrometer via signal cables, and on the basis of computation by the data processing module of the relevant computer software, outputs the mass percentages of O, N, H and Ar in the sample. The lower limit of detection can be below 0.01 ppm to 0.1 ppm, and no less than three elements can be measured simultaneously in one analysis cycle.

7 Claims, 1 Drawing Sheet

PULSE HEATING-TIME OF FLIGHT MASS SPECTROMETRIC GAS ELEMENTS ANALYZER

FIELD OF THE INVENTION

The invention involves the quantitative analysis of chemical composition of materials, and particularly, provides a pulse heating-inert gas fusion—time of flight mass spectrometric gas elements analyzer, which is for analyzing the contents of gas elements such as oxygen (O), nitrogen (N), hydrogen (H) and argon (Ar) in such inorganic materials as metals and ceramics.

BACKGROUND OF THE INVENTION

O, N, H and Ar are extremely important for material performance, and are the key indices in material design, production and application. The quantitative analyzers for O, N and H have been widely used in scientific research and production. Unfortunately, the existing devices don't provide the capability of Ar analysis.

Today, O, N and H analysis is conducted mostly with pulse heating-inert gas fusion—infrared absorption & thermal conductivity analyzer. Its analysis process is as follows: The sample is fused in the graphite crucible of pulse heating electrode furnace, and O in the sample reacts with C in the graphite crucible at a high temperature to produce CO and a little bit $CO_2$, while N and H are released as $N_2$ and $H_2$ at the high temperature. The inert carrier gas sweeps the products out. A non-dispersive infrared detector is used to analyze CO, or to analyze $CO_2$ after all CO is transferred into $CO_2$; a thermal conductivity detector is used for analyzing $N_2$ or $H_2$; thus, O, N and H contents in the sample are figured out through conversion.

The disadvantages of said analyzer are as follows: 1) Trace Ar in the materials can't be measured, and researches prove that Ar in the metal lattice affects the material performance to some extent; 2) The instrument structure, particularly, the gas conduit system, is quite complicated, and the complicated gas transformation or removal method has to be adopted to avoid interference; 3) In the event that the chromatographic column is not used for gas separation after releasing, at most two elements (e.g., O/N or O/H) can be measured at one time for one instrument, in the consecutive manner, not simultaneously; in the event that the chromatographic column is used, the analysis duration has to be prolonged; 4) The sensitivity of some existing instrument is up to 0.1 ppm for H analysis and 1 ppm for the other elements, which can't address the need of various new or special materials for analytical sensitivity.

SUMMARY OF THE INVENTION

The purpose of the invention is to provide a pulse heating—inert gas fusion—time of flight mass spectrometric gas elements analyzer, which adopts a mass spectrometer as detector, and is able to simultaneously analyze multiple elements in one analysis cycle with high sensitivity. It is for analysis of O, N, H and Ar elements in such inorganic materials as metals and ceramics.

The invention comprises of a pulse heating electrode furnace, a sample charging system, a purification device, TOFMS, a signal acquisition and data processing system and an automatic control system, wherein the electrode furnace and sample charging system are united as one via upper/lower electrodes and pneumatic cylinders to form a closed hearth, and jointly enter the sample into the graphite crucible between the upper and the lower electrodes during analysis; said electrode furnace, purification device and TOFMS are interconnected through the gas pipelines: the purified inert carrier gas comes into the hearth from its top, carrying out the gas components released from sample fusion, and upon re-purification, comes into the TOFMS. Said signal acquisition and data processing system is connected to the detector of said mass spectrometer via signal cables for signal acquisition and amplification, and on the basis of computation by the data processing module of the relevant computer software, outputs the mass percentages of O, N, H and Ar in the sample; the voltage and current monitoring meters in said automatic control system are connected through cables to the corresponding electric circuits of said analyzer; the gas pressure and flow monitoring meters are connected through gas pipelines to the corresponding gas pipelines of said analyzer; the automatic control module in said computer software controls the action of the actuating elements such as the pneumatic valve set and electromagnetic valve set according to the pre-configured program, so as to implement the automation of the analysis process.

Said pulse heating electrode furnace comprises of a heating control system, a water cooling system and a furnace body; said furnace body comprises of an upper electrode and lower electrode; both ends of the secondary of the transformer in said heating control system of said electrode furnace are respectively connected with the upper electrode and lower electrode of said furnace body; said water cooling system provides the circulating cooled water to the upper electrode and lower electrode of said furnace body as well as said transformer, and is connected through water pipelines with the upper electrode and lower electrode of said furnace body as well as said transformer, ensuring that said furnace body and said transformer are not overheated during the heating. During sample analysis, said lower pneumatic cylinder pushes the lower electrode, locating the graphite crucible between the upper electrode and lower electrode of said furnace body, and the graphite crucible firmly contacts the upper electrode and lower electrode on both ends; the sample is automatically charged by said sample charging system into the graphite crucible.

Said sample charging system comprises of a sample charging block, a sample charging bar, a pneumaticpneumatic gas source, an upper pneumatic cylinder, a pneumatic valve set and so forth. Said pneumaticpneumatic gas source outputs the pneumaticpneumatic gas of certain pressure via reductor, to drive the pneumatic valve set through the pneumatic gas pipeline. Said pneumatic valve set controls the action of said upper cylinder in the time sequence of the analysis process, and drives the sample charging block and sample charging bar to charge the sample into said graphite crucible for analysis.

Said purification device comprises of a dust filter, a carrier gas purifier, a redox reaction device, gas pipelines, a pressure stabilizer, and a flow stabilizer. The gas transformation device is designed as needed. For instance, when it is necessary to transform all CO into $CO_2$ so as to achieve a better measuring sensitivity, the redox reaction device prior to the mass spectrometer may use a copper oxide furnace or Schutz reagent.

After pressure reduction by the carrier gas reductor, the carrier gas outputs from the carrier gas source, enters the carrier gas purifier for removal of the impurities and moisture, and then passes the gas pipeline into the furnace body for participation in the analysis. After the outgassing post-analysis product is carried out by the carrier gas and enters the dust filter for removal of dust and moisture, and then goes into the inlet of the sample introduction system of the mass spectrometer.

Said TOFMS comprises of a sample introduction capillary, a sample introduction control valve, an electron impact ion source, an acceleration and extraction field, a vacuum chamber, a reflector, a detector, a vacuum pump, and a power source; the invention may also use a linear TOFMS without reflector.

The tip of said sample introduction capillary with a control valve vertically plugs into the center of TOFMS ion source area. An electron gun is located above the ion source area, and the electron beam it emits impacts the sample downwards; on the right of the ion source is the acceleration and extraction field; the ion source, reflector, detector and vacuum pump, which together form a vacuum chamber are separate components connected through flanges to the vacuum chamber from different directions; the outlet of the vacuum chamber is connected through flange to the inlet of the vacuum pump. The power source electrifies the various parts of said mass spectrometer via sealed connectors.

Said signal acquisition and data processing system comprises of an amplifier, a high frequency signal acquisition card, a computer and software.

Said computer controls the pulse heating electrode furnace and sample charging system through cables in the time sequence of analysis, and achieves the heating output and signal feedback of the pulse heating electrode furnace via the feedback loop; the signal output from the mass spectrometer first of all enters the amplification circuit for amplification by the amplifier, and then enters the high frequency signal acquisition card, so that the computer receives the signal and carries out the relevant data processing with the computing module of said software.

Said automatic control system comprises of a heating voltage monitoring meter, a heating current monitoring meter, a carrier gas flow meter, a carrier gas pressure meter, a pneumatic gas pressure meter, a pneumatic valve set and automatic control software.

Said heating voltage monitoring meter is connected through conductive wire to the upper electrode and lower electrode, while heating current monitoring meter is connected through conductive wire to the current transducer; said carrier gas pressure meter and flow meter are connected through gas pipeline to the gas line; said pneumatic gas pressure meter and pneumatic valve set are respectively connected through pneumatic gas pipeline to the pneumatic gas loop; said heating voltage monitoring meter, heating current monitoring meter, carrier gas flow meter, carrier gas pressure meter and pneumatic gas pressure meter are all mounted onto the front panel of the apparatus.

The automatic control module in the computer software controls the operation of the relevant valves of the pneumatic valve set in the time sequence.

The analyzing principle for the pulse heating—time of flight mass spectrometric gas elements analyzer is as follows: In the inert gas environment, the sample is fused in the graphite crucible of the pulse heating electrode furnace, and O in the sample reacts with C in the graphite crucible to produce CO and a little bit $CO_2$; N, H and Ar elements are released as gaseous $N_2$, $H_2$ and Ar at high temperature. The inert carrier gas helium (He) carries the said gas products out, and after purification and filtration, passes the sample introduction capillary leading to the TOFMS; TOFMS records the changes of CO, $N_2$, $H_2$ and Ar ion in the entire process of pulse heating and releasing, and computes the acquired signals with certain mathematic model, to get the contents of O, N, H and Ar in the sample.

In the above process, CuO furnace or Schutz reagent may be used to transform all CO, product of oxidation, into $CO_2$, and the mass spectrometer gets the content of O in the sample by recording $CO_2$ changes; this can improve the sensitivity of O analysis.

In the above process, Ar may be used as carrier gas. In this case, the said element analyzer of the invention can be used to analyze the contents of O, N and H only.

The Invention Provides the Following Advantages Compared with the Prior Arts:

1. The common detector—TOFMS, which is used for quantitative analysis, is suitable for analyzing such elements as O, N, H and Ar, which can be transformed into gaseous components; while the existing devices is suitable for analyzing O, N and H only.

2. The common detector—TOFMS, which is used for quantitative analysis, is capable of analyzing four elements in one analysis cycle; while the existing devices, which adopt the combined quantitative analysis method, mostly combine the infrared absorption detector and thermal conductivity detector, and set the sequence of analysis according to the specific requirements of spectrometric analysis and thermal conductivity analysis, usually can analyze at most two elements in one analysis cycle.

3. For the mass spectrometric analysis technology, the lower limit of detection can be below to 0.1 ppm for all elements; while for the existing methods, the lower limit of detection is just 1 ppm for O and N, except for 0.1 ppm for H.

4. In the invention, the sample introduction technology for the mass spectrometer is capillary branch dispersion: only extremely little gas enters the high vacuum of the mass spectrometer, and the remaining carrier gas is all discharged; the gas conduit system is relatively simple, and multiple components can be measured in one analysis cycle with high sensitivity. In the existing methods, the sample introduction for both infrared sensor and thermal conductivity cell is flow type, and all carrier gas must flow though the detection tank and no leakage is allowed.

DETAILED DESCRIPTION OF THE EMBODIMENTS

Figure 1:
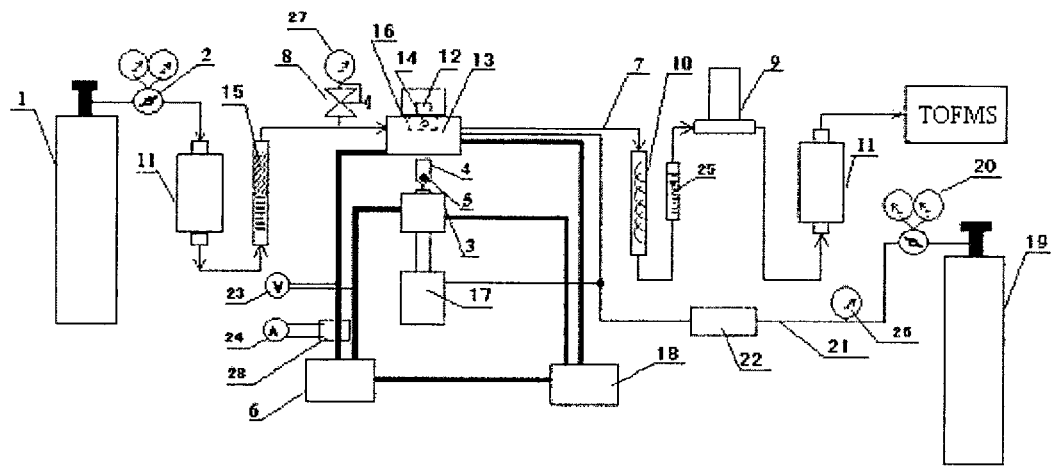
FIG. 1 shows the structure diagram of said pulse heating—time of flight mass spectrometric gas elements analyzer of the invention, which includes the carrier gas (highly pure argon gas or helium gas) steel tank 1, reductor 2, lower electrode 3, graphite crucible 4, sample to be tested 5, heating control system 6, analytical gas line 7, pressure stabilizer 8, flow stabilizer 9, dust filter 10, redox reaction furnace 11, sample charging block 12, upper electrode 13, sample charging bar 14, carrier gas purifier 15, upper pneumatic cylinder 16, lower pneumatic cylinder 17, water cooling system 18, pneumatic gas source 19, pneumatic gas reductor 20, pneumaticpneumatic gas pipeline 21, pneumatic valve set 22, voltage meter 23, current meter 24, flow meter 25, pneumatic gas pressure meter 26, carrier gas pressure meter 27 and current transducer 28.
Figure 2:
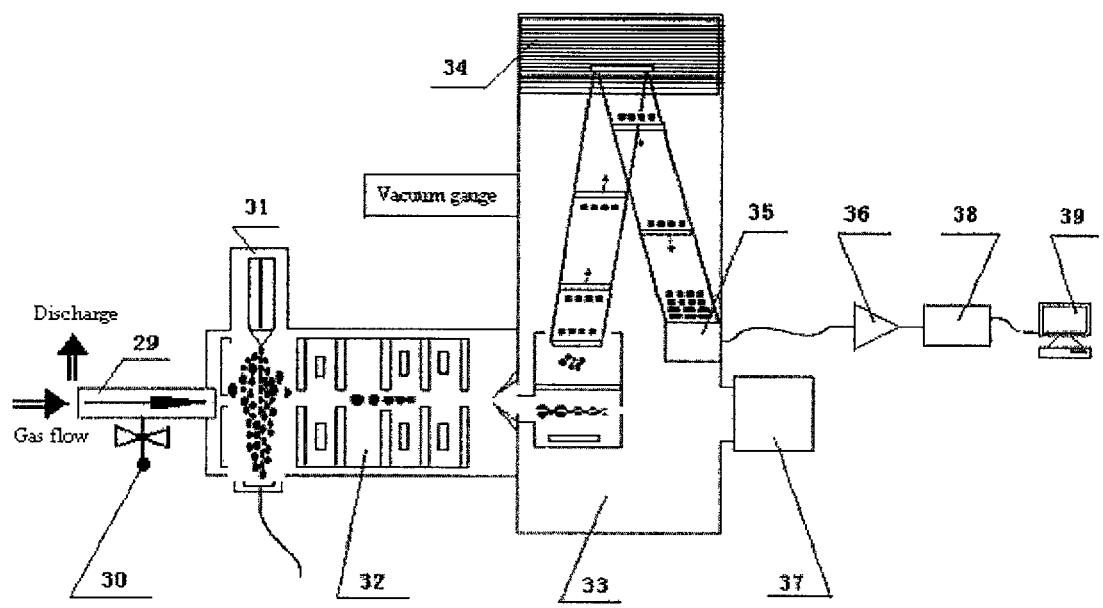
FIG. 2 shows the structure diagram of said TOFMS of the invention, which includes the sample introduction capillary 29, sample introduction control valve 30, electron impact ion source 31, acceleration and extraction field 32, vacuum chamber 33, reflector 34, detector 35, amplifier 36, high vacuum pump 37, high frequency signal acquisition card 38 and computer 39.

FIGS. 1 and 2 shows a specific embodiment of the invention.

The pulse heating electrode furnace comprises of a heating control system 6, a water cooling system 18 and a furnace body. Said furnace body comprises of an upper electrode 13 and lower electrode 3; both ends of the secondary of the transformer in said heating control system of said electrode furnace are respectively connected with the upper electrode 13 and lower electrode 3 of said furnace body; said water cooling system 18 which provides the circulating cooled water to the upper electrode 13 and lower electrode 3 of said furnace body as well as said transformer, is connected through water pipelines with the upper electrode 13 and lower electrode 3 of said furnace body as well as said transformer, ensuring that said furnace body and said transformer are not overheated during the heating. During sample analysis, said lower pneumatic cylinder 17 pushes the lower electrode 3, locating the graphite crucible 4 which is on the lower electrode 3 between the upper electrode 13 and lower electrode 3 of said furnace body, and the graphite crucible firmly contacts the upper electrode 13 and lower electrode 3 on both ends; the sample 5 is automatically charged by said sample charging system into the graphite crucible 4.

Said sample charging system comprises of a sample charging block 12, a sample charging bar 14, a pneumatic gas source 19, a upper pneumatic cylinder 16, a pneumatic valve set 22 and so forth; said pneumatic gas source 19 outputs the pneumatic gas of certain pressure via reductor 20, to drive the pneumatic valve set 22 through the pneumatic gas pipeline 21; said pneumatic valve set 22 controls the action of said upper pneumatic cylinder 16 in the time sequence of the analysis process, and pushes the sample charging block 12 and sample charging bar 14 to charge the sample 5 into said graphite crucible 4 for analysis.

Said purification device comprises of a dust filter 10, a carrier gas purifier 15, a redox reaction device 11, gas pipeline 7, a pressure stabilizer 8, and a flow stabilizer 9. The gas transformation device is designed as needed. For instance, when it is necessary to transform all CO into $CO_2$ to achieve a better measuring sensitivity, the redox reaction device 11 prior to the mass spectrometer may use a copper oxide furnace or Schutz reagent. After pressure reduction by the carrier gas reductor 2, the carrier gas outputs from the carrier gas source 1, enters said redox reaction device 11 and the carrier gas purifier 15 for removal of the impurities and moisture, and then passes the gas pipeline 7 into the furnace body for participation in the analysis. After outgassing the post-analysis product is carried out by the carrier gas and enters the dust filter 10 for removal of dust and moisture, and then goes into the inlet of the sample introduction system of the mass spectrometer 29. If necessary it will passes the redox reaction device 11 before goes into the mass spectrometer.

Said TOFMS comprises of a sample introduction capillary 29, a sample introduction control valve 30, an electron impact ion source 31, an acceleration and extraction field 32, a vacuum chamber 33, a reflector 34, a detector 35, a vacuum pump 37, and a power source 40. The invention may also adopt the linear TOFMS without reflector. The tip of said sample introduction capillary 29 with a control valve 30 vertically plugs into the center of TOFMS ion source 31 area; the electron gun is located above the ion source 31 area, and the electron beam emitted from the electron gun impacts the sample downwards; on the right of the ion source 31 is the acceleration and extraction field 32; the ion source 31, reflector 34, detector 35 and vacuum pump 37 together form a vacuum chamber; the ion source 31, reflector 34 and detector 35, which are individual components, are connected through flanges to the vacuum chamber 33 from different directions; the outlet of the vacuum chamber 33 is connected through flange to the inlet of the vacuum pump 37. The power source 40 electrifies various parts of said mass spectrometer via sealed connectors.

Said signal acquisition and data processing system comprises of an amplifier 36, a high frequency signal acquisition card 38, a computer 39 and software 41; said computer controls the pulse heating electrode furnace and sample charging system through cables in the time sequence of analysis, and simultaneously achieves the heating output and signal feedback of the electrode furnace via the feedback loop; the signal output from the mass spectrometer first of all enters the amplification circuit for amplification by the amplifier 36, and then enters the high frequency signal acquisition card 38, so that the computer receives the signal and carries out the relevant data processing with the computing module of said software 41.

Said automatic control system comprises of a heating voltage monitoring meter 23, a heating current monitoring meter 24, a carrier gas flow meter 25, a carrier gas pressure meter 27, a pneumatic gas pressure meter 26, a pneumatic valve set 22 and automatic control module of software 41.

Said heating voltage monitoring meter 23 is connected through conductive wire to the upper electrode 13 and lower electrode 3, while said heating current monitoring meter 24 is connected through conductive wire to the current transducer 28; said carrier gas pressure meter 27 and flow meter 25 are connected through gas pipeline 7 to the analytical gas conduit; said pneumatic gas pressure meter 26 and pneumatic valve set 22 are respectively connected through pneumatic gas pipeline 21 to the pneumatic gas loop; said heating voltage monitoring meter 23, heating current monitoring meter 24, carrier gas flow meter 25, carrier gas pressure meter 27 and pneumatic gas pressure meter 26 are all mounted onto the front panel of the apparatus.

The automatic control modules of said computer software 41 control the actions of the corresponding valves in the pneumatic valve set 22 in the time sequence.

The invention involves a pulse heating-inert gas fusion—time of flight mass spectrometric gas elements analyzer, which gets the contents of the gas elements in the sample by mass spectrometric analysis of the transformation products of the elements as well as the quantitative relations in element transformation.

The steps of analysis are as follows:

(1) The pulse heating electrode furnace, sample charging system, purification device, TOFMS, signal acquisition and data processing system and automatic control system are interconnected in the manner described above. The inert carrier gas is provided into the electrode furnace.

(2) Set the parameters of said instrument: pressure and flow rate of carrier gas, outgassing, purging and analysing time, heating voltage and current, and mass spectrometric introduction dosage.

(3) Under the above-mentioned operating conditions, the standard samples or reference materials with known element contents or standard gas mix with known composition are used to draw the operating curves;

(4) Process and weigh the sample;

(5) Start the heating, and purge the electrode furnace, graphite crucible and gas conduit system with the carrier gas;

(6) Charge the sample;

(7) Record the changes of signal strength of the relevant mass spectrometric analysis line to time during the entire process of sample fusion and releasing; and (8) Conduct signal processing with certain mathematic model, comparing with the operating curve, and compute and output the contents of the elements in the sample to be tested.

The invention claimed is:

1. A pulse heating-inert gas fusion—time of flight mass spectrometric gas elements analyzer, comprising of a pulse heating electrode furnace, a sample charging system, a purification device, TOFMS, a signal acquisition and data processing system and an automatic control system, characterized in that said electrode furnace and sample charging system are united as one via upper/lower electrodes and upper/lower pneumatic cylinders to form a closed hearth, and jointly enter the sample into the graphite crucible between the upper and lower electrodes during analysis; said electrode furnace, purification device and time-of-flight mass spectrometer (TOFMS) are interconnected through the gas pipelines: the purified inert carrier gas comes into the hearth from its top, carrying out the gas components released from sample fusion, and upon re-purification, comes into the TOFMS; said signal acquisition and data processing system is connected to the detector of said mass spectrometer via signal cables for signal acquisition and amplification, and on the basis of computation by the data processing module of the computer software, outputs the mass percentages of O, N, H and Ar in the sample; the voltage and current monitoring meters in said automatic control system are connected through cables to the corresponding electric circuits of said analyzer; the gas pressure and gas flow monitoring meters are connected through gas pipelines to the corresponding gas pipelines of said analyzer; the automatic control module in said computer software controls the action of the actuating elements such as the pneumatic valve set and electromagnetic valve set according to the pre-configured program, so as to implement the automation of the analysis process.

2. The analyzer of claim 1, characterized in that said pulse heating electrode furnace comprises of a heating control system (6), a water cooling system (18) and a furnace body; said furnace body comprises of an upper electrode (13) and lower electrode (3); both ends of the secondary of the transformer in said heating control system of said electrode furnace are respectively connected with the upper electrode (13) and lower electrode (3) of said furnace body; said water cooling system (18) which provides the circulating cooled water to the upper electrode (13) and lower electrode (3) of said furnace body as well as said transformer is connected through water pipelines with the upper electrode (13) and lower electrode (3) of said furnace body as well as said transformer, ensuring that said furnace body and said transformer are not overheated during the heating; during sample analysis, said lower cylinder (17) pushes the lower electrode (3), locating the graphite crucible (4) which is on the lower electrode (3) between the upper electrode (13) and lower electrode (3) of said furnace body, and the graphite crucible firmly contacts the upper electrode (13) and lower electrode (3) on both ends; the sample (5) is automatically charged by said sample charging system into the graphite crucible (4).

3. The analyzer of claim 1, characterized in that said sample charging system comprises of a sample charging block (12), a sample charging bar (14), a pneumatic gas source (19), a upper pneumatic cylinder (16), a pneumatic valve set (22) and so forth; said pneumatic gas source (19) outputs the pneumatic gas of certain pressure via reductor (20), to drive the pneumatic valve set (22) through the pneumatic gas pipeline (21); said pneumatic valve set (22) controls the action of said upper pneumatic cylinder (16) in the time sequence of the analysis process, and drives the sample charging block (12) and sample charging bar (14) to charge the sample (5) into said graphite crucible (4) for analysis.

4. The analyzer of claim 1, characterized in that said purification device comprises of a dust filter (10), a carrier gas purifier (15), a redox reaction device (11), gas pipeline (7), a pressure stabilizer (8), and a flow stabilizer (9); after pressure reduction by the carrier gas reductor (2), the carrier gas outputs from the carrier gas source (1), enters said redox reaction device (11) and the carrier gas purifier (15) for removal of the impurities and moisture, and then passes the gas pipeline (7) into the furnace body for participation in the analysis; after outgassing the post-analysis product is carried out by the carrier gas and enters the dust filter (10) for removal of dust and moisture, and then goes into the inlet of the sample introduction system (29) of the mass spectrometer; if necessary it will passes the redox reaction device 11 before goes into the mass spectrometer.

5. The analyzer of claim 1, characterized in that said TOFMS comprises of a sample introduction capillary (29), a sample introduction control valve (30), an electron impact ion source (31), an acceleration and extraction field (32), a vacuum chamber (33), reflector (34), a detector (35), a vacuum pump (37), and a power source (40), the tip of said sample introduction capillary (29) with a control valve (30) vertically plugs into the center of TOFMS ion source (31) area; the electron gun is located above the ion source (31) area, and the electron beam that it emits impacts the sample downwards; on the right of the ion source (31) is the acceleration and extraction field (32); the ion source (31), reflector (34), detector (35) and vacuum pump (37) which together form a vacuum chamber; the ion source (31), reflector (34) and detector (35) are connected through flanges to the vacuum chamber (33) from different directions; the outlet of the vacuum chamber (33) is connected through flange to the inlet of the vacuum pump (37); the power source (40) electrifies various parts of said mass spectrometer via sealed connectors.

6. The analyzer of claim 1, characterized in that said signal acquisition and data processing system comprises of an amplifier (36), a high frequency signal acquisition card (38), a computer (39) and software (41); said computer controls the pulse heating electrode furnace and sample charging system through cables in the time sequence of analysis, and achieves the heating output and signal feedback of the electrode furnace via the feedback loop; the signal output from the mass spectrometer first of all enters the amplification circuit for amplification by the amplifier (36), and then enters the high frequency signal acquisition card (38), so that the computer receives the signal and carries out the relevant data processing with the computing module of said software (41).

7. The analyzer of claim 1, characterized in that said automatic control system comprises of a heating voltage monitoring meter (23), a heating current monitoring meter (24), a carrier gas flow meter (25), a carrier gas pressure meter (27), a pneumatic gas pressure meter (26), a pneumatic valve set (22) and automatic control module of software (41); said heating voltage monitoring meter (23) is connected through conductive wire to the upper electrode (13) and lower electrode (3), while said heating current monitoring meter (24) is connected through conductive wire to the current transducer (28); said carrier gas pressure meter (27) and flow meter (25) are connected through gas pipeline (7) to the analytical gas line; said pneumatic gas pressure meter (26) and pneumatic valve set (22) are respectively connected through pneumatic gas pipeline (21) to the pneumatic gas loop; said heating voltage monitoring meter (23), heating current monitoring meter (24), carrier gas flow meter (25), carrier gas pressure meter (27) and pneumatic gas pressure meter (26) are all mounted onto the front panel of the apparatus.

* * * * *

UNITED STATES PATENT AND TRADEMARK OFFICE
CERTIFICATE OF CORRECTION

PATENT NO.       : 7,847,242 B2
APPLICATION NO.  : 12/259502
DATED            : December 7, 2010
INVENTOR(S)      : Haizhou Wang et al.

It is certified that error appears in the above-identified patent and that said Letters Patent is hereby corrected as shown below:

On the Title Page, Item (75)

The third inventor's name should be "Xuejing SHEN", not "Xuejing Yang".

Signed and Sealed this
Twenty-fifth Day of January, 2011

David J. Kappos
*Director of the United States Patent and Trademark Office*